United States Patent [19]

Bunger et al.

[11] Patent Number: 5,739,423
[45] Date of Patent: *Apr. 14, 1998

[54] METHOD FOR DETERMINING THERMODYNAMIC AND MOLECULAR PROPERTIES IN THE LIQUID PHASE

[75] Inventors: James W. Bunger; Christopher P. Russell; Prasad A. V. Devineni, all of Salt Lake City, Utah

[73] Assignee: James W. Bunger and Associates, Inc., Salt Lake City, Utah

[*] Notice: The term of this patent shall not extend beyond the expiration date of Pat. No. 5,574,215.

[21] Appl. No.: 748,133

[22] Filed: Nov. 12, 1996

Related U.S. Application Data

[63] Continuation of Ser. No. 396,378, Feb. 28, 1995, Pat. No. 5,574,215, which is a continuation-in-part of Ser. No. 204,553, Mar. 1, 1994, abandoned.

[51] Int. Cl.$^6$ .................................................. G01N 33/00
[52] U.S. Cl. ............................................ 73/64.54; 422/68.1
[58] Field of Search ................................ 73/64.54, 64.45, 73/61.41, 61.43, 61.76; 422/68.1

[56] References Cited

U.S. PATENT DOCUMENTS 5,341,672  8/1994  Kawanami et al. ................. 73/64.54
5,574,215  11/1996  Bunger et al. ...................... 73/64.54

*Primary Examiner*—Michael Brock
*Attorney, Agent, or Firm*—James L. Sonntag

[57] ABSTRACT

A method for calculating the average aggregate mass of individual molecules in a sample, where the molecules in solution associate to form clusters. Data sets of average aggregate mass of the sample versus concentration of the sample in the solvent are generated. The basic principles and technology in generation of the data is the well understood action of a solute upon the solvent vapor pressure above the solution. By observing the effect of a sample solute on the temperature/vapor pressure properties of a solvent, if is possible by known methods to determine its average aggregate mass. When dealing with a solute material that tends to form clusters, however, the average aggregate mass found is an apparent average aggregate mass, i.e. the average aggregate mass of all of the particles, which are the clusters and any unassociated molecules, if any. To determine the true average aggregate mass, a method employing the determined apparent average aggregate masses, referred to herein as the BRD method, is used. Since the method is based upon cluster thermodynamics and equilibrium properties, it reflects more accurately the behavior of the clusters at various dilutions. The method provides a basis for the prediction of thermodynamic and equilibrium properties, which was not possible with previous methods.

12 Claims, 4 Drawing Sheets

Results of BRD Model to Characterize
Molecular Association Thermodynamics

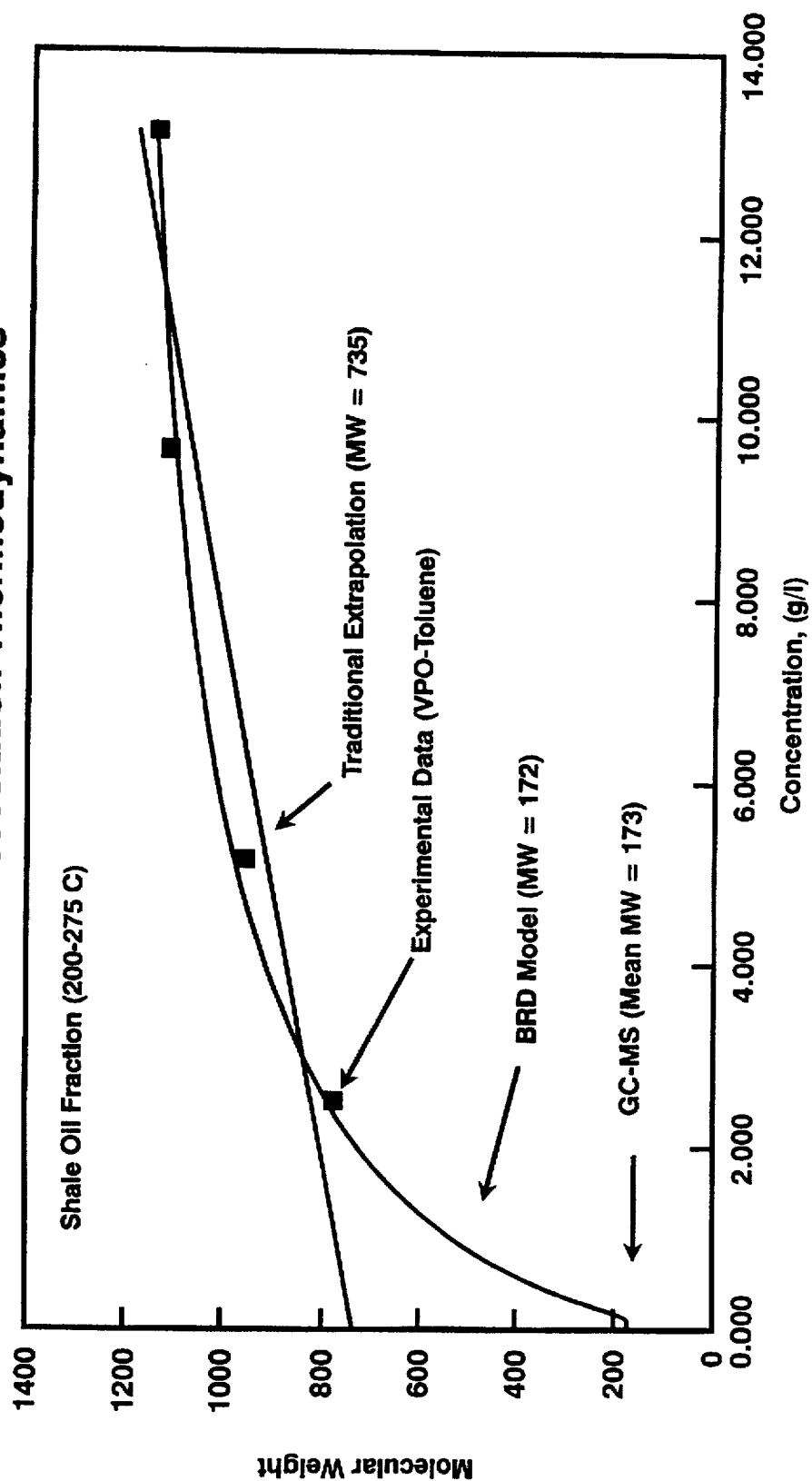

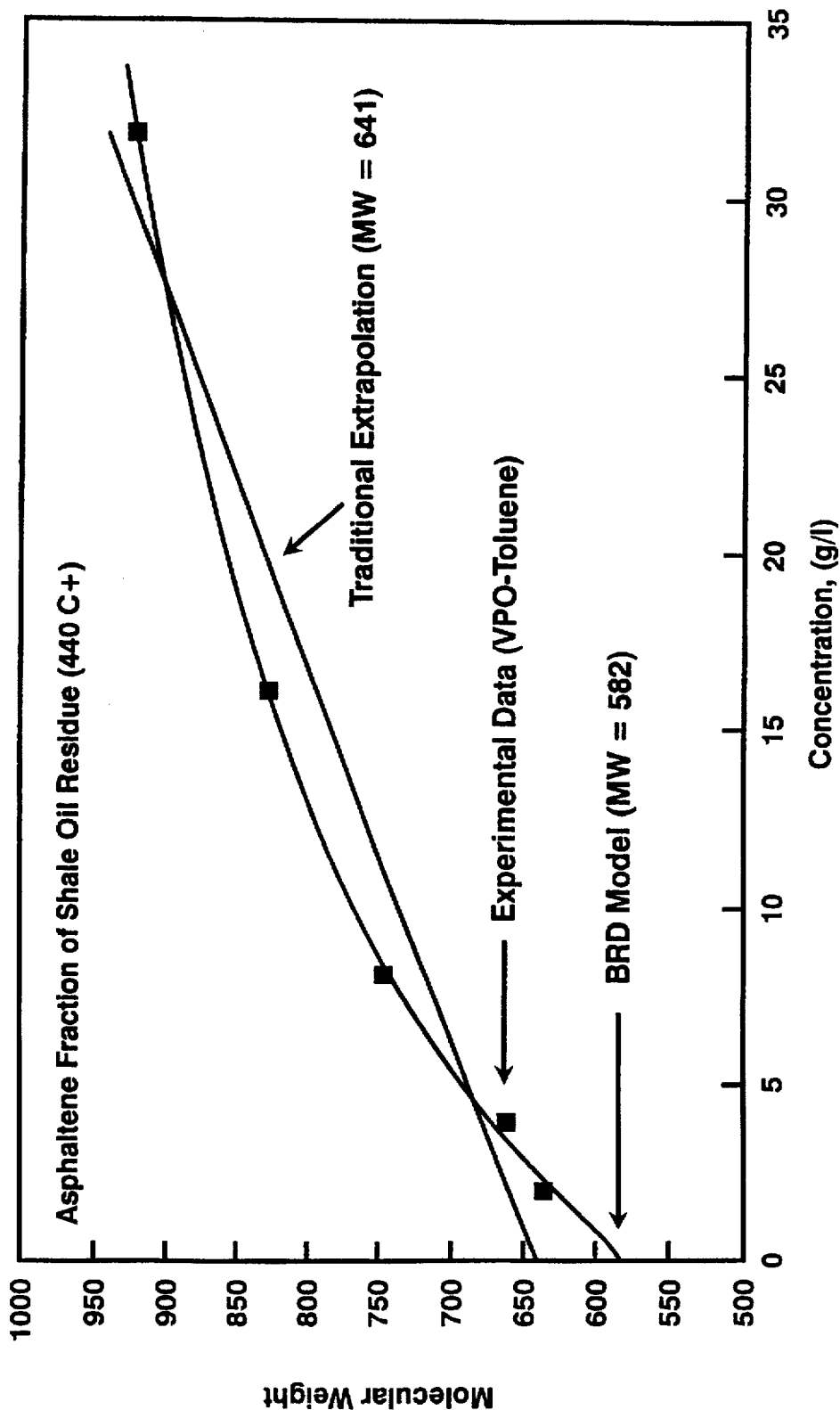

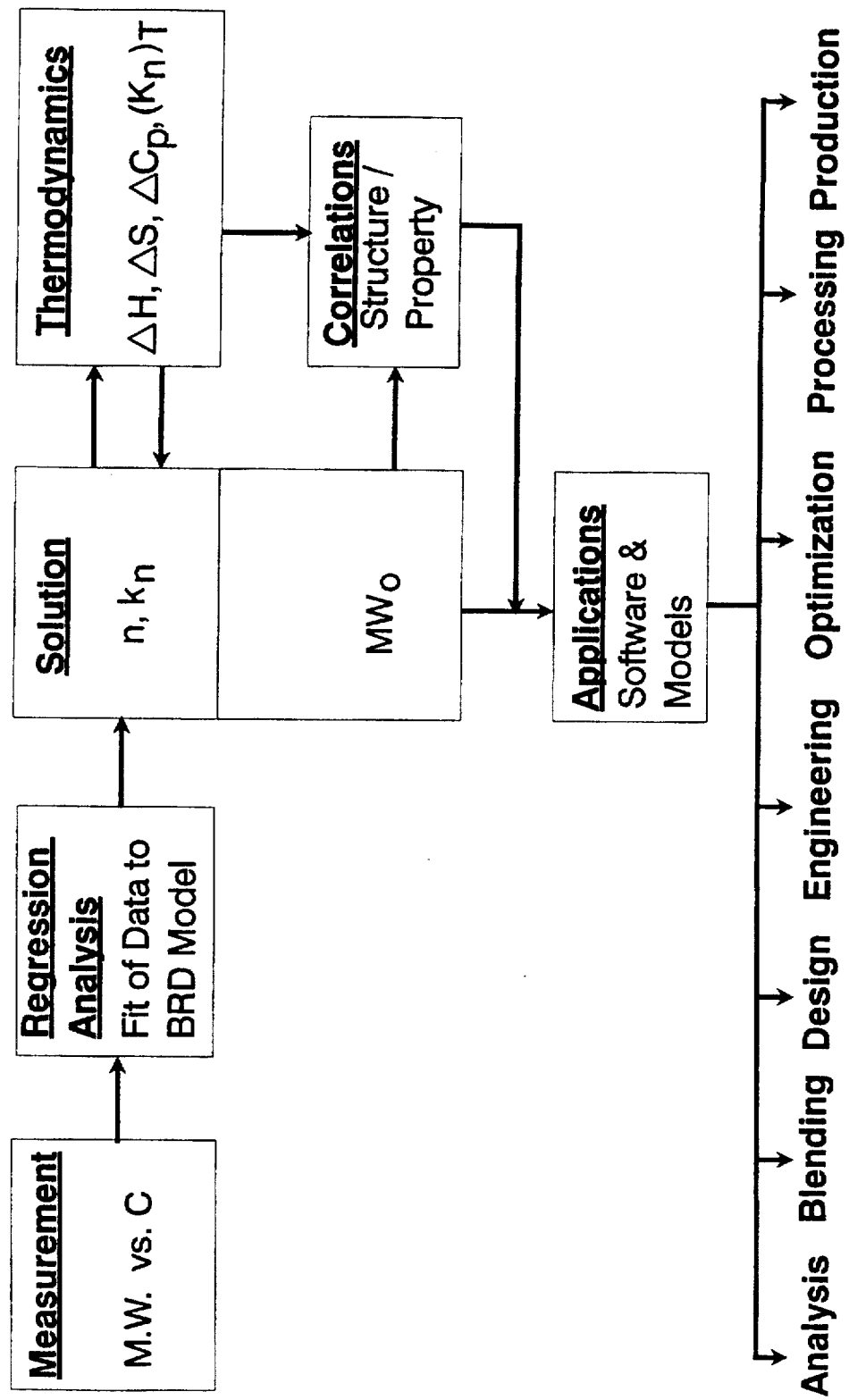

METHOD FOR DETERMINING THERMODYNAMIC AND MOLECULAR PROPERTIES IN THE LIQUID PHASE

RELATED APPLICATIONS

This application a continuation of U.S. patent application Ser. No. 08/396,378, filed Feb. 28, 1995, now U.S. Pat. No. 5,574,215, issued Nov. 12, 1996 which is a is a continuation in part from U.S. patent application Ser. No. 08/204,553, filed Mar. 1, 1994, now abandoned.

STATEMENT OF GOVERNMENT INTEREST

This invention was made in part with United States Government support under contract No. #DE-AC21-93MC29240 awarded by the DOE. The government may have certain rights in this invention.

FIELD OF THE INVENTION

This invention relates to measurement of thermodynamic and molecular properties.

BACKGROUND OF THE INVENTION

The molecular composition and chemistry of high-molecular weight multicomponent mixtures is difficult to study. As used to herein, "high-molecular weight" refers to those molecules possessing a molecular weight over about 250 Dalton (atomic mass units). As molecular weight increases, the number of possible structures increases exponentially and, at some point, the ability to identify individual constituents breaks down. The problem is compounded by the fact that as molecular weight increases, volatility decreases, thereby limiting the application of techniques such as gas chromatography to separate components by their thermodynamic properties in the unassociated (ideal) state. The ability to extend such techniques to higher molecular weight is further limited by the thermal stability of the molecules which change structures at excessive temperatures. Thus, a limitation of the analysis of higher molecular weight components is that such studies must be conducted on these systems in the condensed state.

In the condensed state, two or more molecules may associate by electronic attractions (polar, van der Waal's, electron donor-acceptor, etc.) into clusters of molecules. The total number of monomers plus the total number of clusters is defined as the total number of particles. When association occurs, the number of particles is reduced and the average size of the particles is increased compared to the totally dissociated (monomeric) state.

The association of molecules in the condensed state adds a new complication to the study of composition and chemistry. Intermolecular associations interfere with separations and cause behavioral changes that can mask the true molecular composition.

That such behavior has served to confuse the scientific community about the composition and chemistry of high-molecular weight species, can be readily shown by examination of the published literature regarding asphaltenes. (See Bunger, J. W. and Li, N. C., Chemistry of Asphaltenes, Advances in Chemistry Series, ACS, 195 (1981); Winniford, R. S., "The Evidence for Association of Asphaltenes in Dilute Solutions," J. of Inst. of Pet., 49, pp. 215–221, July (1963); Speight, J. G., "Influence of Temperature and Solvent on the Precipitation of Asphaltenes," Fuel Science and Tech. Interntl., 8, 6 (1990); Yen, T. F., "The Colloidal Aspects of a Macrostructure of Petroleum Asphalt", Fuel Science Technology International, 10, 723–734 (1992); Cooper, A. K., Determination of Molecular Weight, Chemical Analysis Science, 103, John Wiley and Son, New York (1989).

Asphaltenes are defined as those species which precipitate from solution, and to date, there is no general agreement as to the structural features or even the size of the molecules which make up asphaltenes, even when the study is restricted to a common starting material.

The thermodynamics of association, whether self-association as in condensation or precipitation of like species, or intermolecular association as in condensation, precipitation or adsorption of unlike species strongly influence the liquid phase behavior. In spite of the general recognition of the importance of thermodynamics in these associations, there remains a need for a methodology to quantify these properties in a manner meaningful at the molecular level. The present invention describes a method that can be used to determine the condition of molecules in the associated state in thermodynamic terms generally recognized within the scientific community. The invention involves in part a mathematical method named the Bunget-Russell-Devineni Molecular Association Thermodynamic Method, or BRD method.

OBJECTS OF THE INVENTION

It is, therefore, an object of the invention to provide a method for calculating thermodynamic and molecular properties in a solution.

Further objects of the invention will become evident in the description below.

SUMMARY OF THE INVENTION

An embodiment of the invention is a method for calculating the average molecular weight of individual molecules ($MW_O$) in a sample, where the molecules in solution associate to form clusters, which method comprises, (a) heating a reference portion of a solvent at a reference temperature ($T_R$) to form a saturated solvent vapor at vapor pressure ($P_R$) above the reference portion, (b) dissolving a measured mass of the sample in a measured second portion of the solvent to provide a solution with a known concentration (C) of the sample in terms of mass per unit volume, and heating a sample portion of the solution to a sample temperature ($T_S$) to form a saturated solvent vapor above the sample portion at vapor pressure ($P_S$), (c) measuring the deviation of the sample temperature and vapor pressure ($T_S$, $P_S$) from the reference temperature and vapor pressure ($T_R$, $P_R$), and computing an apparent molar concentration ($C_M$) in moles per unit volume by reference to the deviation, the apparent concentration being the molar concentration of the clusters of associated molecules and any unassociated molecules, (d) computing an apparent molecular weight (MW) from the equation;

$$MW = \frac{C}{C_M}$$

the apparent molecular weight being the average molecular weight of clusters of associated molecules and any unassociated molecules, (e) repeating steps (a) through (d) for m repetitions with a different value of concentration (C) for each repetition, (f) solving for $a_1, a_2, \ldots a_j$, and $MW_0$ from the MW and C data sets from the following set of equations;

$$R_n = \frac{nk_n}{(MW_o)^{n-1}} Y^n C^{n-1}$$

a set of equations for n=2 to m $$1 - Y = \sum_{i=2}^{m} \frac{ik_i}{(MW_o)^{i-1}} Y^i C^{i-1}$$

$$MW = \frac{MW}{Y + \sum_{i=2}^{m} \frac{R_i}{i}}$$

and a set of equations that are relations between $k_n$ and n, for n=2 to m $$k_n = f(n, a_1, a_2, \ldots, a_j)$$

where m is an integer greater than 2, $a_1, a_2, \ldots a_j$ are constants, and j is an integer greater than 0,
the number of the of apparent molecular weight (MW) versus concentration (C) data points produced by the repetitions in step (e) being an integer greater than j.

Steps (a) through (e) involve generation of points of data for the material being tested. The data sets are apparent molecular weight of the sample (MW) vs. concentration of the sample in a solvent (C). The basic principles and technology in generation of the data is the well understood action of a solute upon the solvent vapor pressure above the solution. In general, the presence of the solute in the solvent reduces the tendency of the solvent to evaporate into the vapor phase. Accordingly, at equal temperatures, the solvent vapor pressure above a solvent with solute will be lower than that above the same solvent without the solute. In addition, in order to bring the vapor pressure of the solution to be equal with that of the pure solvent, the temperature of solution must be raised. This effect can quantified for a particular solvent by application of theory and/or by known calibration techniques using a reference solute with a known molecular weight in solvent. Calibration using a reference of known molecular weight is practiced because the change in vapor pressure is primarily dependent upon the number of moles, i.e., particles, in the solution, and not upon the specific chemical nature of the solute molecule or molecules. Accordingly, by observing the effect of a sample solute on the temperature/vapor pressure properties of a solvent, it is possible by known methods to determine it molecular weight. When dealing with a solute materials that tend to form clusters, the molecular weight found is an apparent molecular weigh, i.e., the average molecular weight of all the particles, which are the clusters and any unassociated molecules, if any. Thus if the solute is highly associated, the apparent molecular weight found will be much higher than the average molecular weight of the solute molecules individually.

Recognizing this problem, practitioners have generated apparent molecular weight vs. concentration data at differing concentrations and extrapolated the data to a zero concentration, the reasoning being that at high dilution, the molecules in solution are more likely to be monomers and not be in clusters. Known mathematical extrapolation methods, particularly linear interpolation methods, have been used. While this method has been moderately successful in determining the molecular weight of the individual molecules for many systems, it is still inadequate. Many solvent systems remain highly associated at high dilution, and as the concentration of the solute approaches zero the relationship between the concentration and the association into clusters is often very non-linear. Accordingly, extrapolation by linear techniques do not comprehend this non-linearity at low concentration and will not accurately determine the molecular weight. In addition, since mathematical extrapolation techniques have no relation to the chemical properties of the system, the extrapolation does not truly reflect the chemical properties of the system and cannot provide any basis for prediction of properties of the molecules other than the molecular weight. Such properties include thermodynamic properties, equilibrium relationships, and the like, and are essential in the understanding of the behavior of the solutions in various process environments, such as blending, precipitation, and in engineering design.

Accordingly, the method process has met the deficiencies of the prior-art methods, by (1) providing a more accurate measure of the molecular weight of individual molecules in associated systems by providing a methodology that is derived from chemical properties of the solution, and (2) providing a method for prediction of thermodynamic properties. Instead of a purely empirical technique, a method, referred to herein as the BRD method, which is derived from chemical thermodynamic principles, is used to determine the molecular weight. In addition, since the method is based upon cluster thermodynamics and equilibrium properties, it reflects more accurately the behavior of the clusters at various dilutions. Thus, the method provides a basis for the prediction of thermodynamic and equilibrium properties, which was not possible with previous methods.

BRIEF DESCRIPTION OF THE DRAWINGS

FIGS. 1, 2 and 3 are graphs of apparent molecular weight vs. concentration showing data points measured by a vapor pressure osmometry (VPO), a solution by the method of the invention, and a linear solution according to the prior art.

FIG. 4 is a flow sheet illustrating the invention.

DETAILED DESCRIPTION OF THE INVENTION

Figure 1:
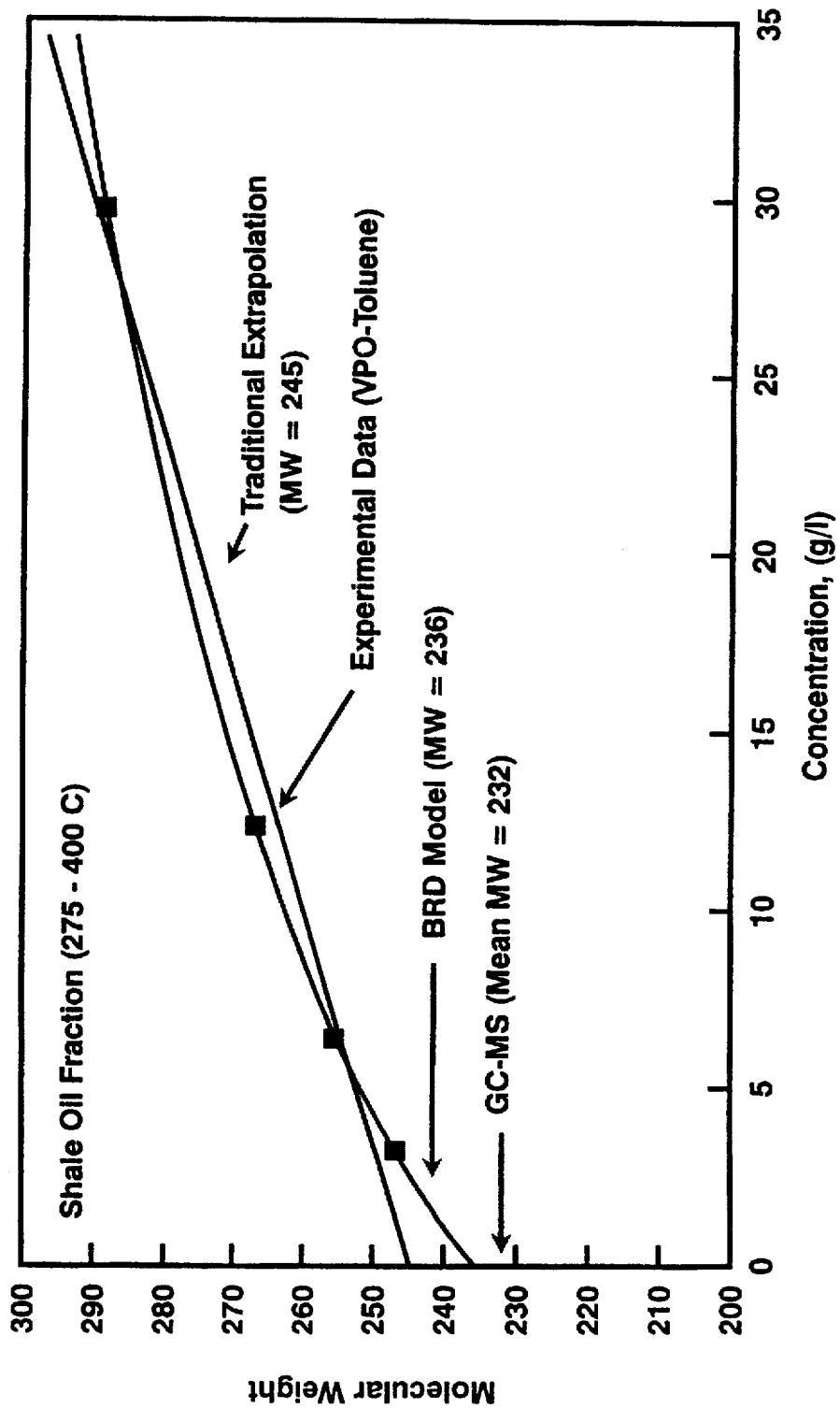

Any method for the determination of the average molecular weight (relative molecular mass) that relies upon the effect of the number of moles of a dissolved material upon solvent temperature vs. vapor pressure properties is suitable. This can be accomplished by, for example, heating a reference portion of the pure solvent used to dissolve the sample, to a reference temperature $(T_R)$ under condition wherein the solvent is in equilibrium with the vapor. By "pure" is meant a solvent without any substantial amounts of the solute. If reference temperature $(T_R)$ is the same as the sample temperature $(T_S)$ the apparent molar concentration $(C_M)$ can be determined from depression the vapor pressure depression $(P_R-P_S)$ resulting from the sample dissolved in the solvent.

Alternately, the reference temperature $(T_R)$ can be such that it provides a reference vapor pressure $(P_R)$ than is equal to the sample vapor pressure $(P_S)$. In this case the apparent molar concentration $(C_M)$ is determined by measuring the rise in the equilibrium temperature $(T_S-T_R)$ resulting from the sample dissolved in the solution. In the most common procedures a portion of the solvent, the reference, and the solution sample are heated to the same temperature $(T_R)$ in a common chamber under conditions of equilibrium between the solvent vapor and the reference portion. Since the solution has a lower vapor pressure, vapor will condense on the solution sample which causes the solution sample to be warmed by the heat of condensation from $T_R$ to $T_S$. The temperature difference between $T_S$ and $T_R$ is commonly measured using thermistors as a difference of resistance ($\Delta R$) between two thermistors in contact with the sample portion and the reference portion, respectively. The thermistors are calibrated to relate the resistance ($\Delta R$) to molar concentration by a series of standard solutions of a solute of known molecular weight in the solvent of the samples being tested.

The most common method for producing apparent molecular weight v. concentration data is that described in ASTM Standard D 2503 (American Society for Testing a Materials, Philadelphia, Pa.). This method is commonly referred to as vapor pressure osmometry (VPO) method. In summary, this method comprises dissolving a weighed portion of a sample in a known quantity of an appropriate solvent. A drop of this solution and a drop of the solvent are suspended, side by side, on separate thermistors in a closed solvent chamber saturated with solvent vapor. Since the vapor pressure of the solution is lower than that of the solvent, solvent condenses on the sample drop and causes a temperature difference between the two drops. The resultant change in temperature is measured using thermometric methods and used to determine the molecular weight of the sample by reference to a previously prepared calibration curve.

Solvents that do not react with the sample should be used. Benzene is the most preferred solvent, but other solvents, such as chloroform, and 1,1,1-trichloroethane have been used. The sample must be completely soluble in the selected solvent at concentrations of at least 0.10M, and it must not have an appreciable vapor pressure at the test temperature.

A calibration curve is prepared for each lot of solvent using a pure compound whose molecular weight is accurately known. Compounds that have been used successfully are benzil, n-octadecane, and squalane. Standard solutions of the calibrating compound in the solvent are prepared. The solvent is placed in a solvent cup in a thermal block in the solvent chamber and the block, solvent and chamber is heated to 37° C. and an equilibrium is established between the liquid solvent and the vapor. Syringes are prepared with the pure solvent and the standard solutions and placed in the thermal block. After the solvent chamber is at equilibrium, the thermistor circuit is calibrated to zero. Below the syringes containing the pure solvent and standard solution are the reference thermistor and sample thermistor, respectively, upon which is deposited a drop of solvent or solution from the respective syringes. The reference thermistor is calibrated to zero by first comparing its resistance with the sample thermistor with a drop of pure solvent on both. After calibration, drops of the pure solvent and standard solutions are then in turn deposited upon the respective thermistors and the difference is resistance, $\Delta R$, is noted. After obtain several $\Delta R$ values vs. concentration, a calibration curve is then prepared by plotting the $\Delta R$ values vs. the molarity.

To measure the molecular weight of a sample, the solvent chamber is prepared as described above by placing the solvent in the solvent cup and bringing the solvent chamber to thermal equilibrium. A solution of known concentration is prepared by dissolving a known weight of the sample in a known volume of the solvent. A drop of the sample solution is deposited from a syringe upon a sample thermistor and the resistance difference, $\Delta R$, between the sample thermistor and the reference thermistor is measured. By reference to the calibration curve, the molarity corresponding to the observed $\Delta R$ value is determined.

Once the molarity, i.e., the number of particles per volume, is determined, the apparent molecular weight (MW) is determined from the following equation;

$$MW = \frac{C}{C_M} \qquad 1)$$

where C=concentration of the sample solute in solution in g/L, and $C_M$=the apparent molar concentration (molarity) of the sample in solution, in m/L. With plurality of data sets of apparent molecular weight (MW) v. concentration (C), using the BRD method the parameters in equations are determined so that molecular weight as one of the parameters is obtained. Apparent molecular weight (MW) is also referred to herein as average aggregate mass ($M_A$).

Mathematical and Chemical Description and Derivation of the BRD Method

Define a generic molecule B which, in the condensed phase partially associates into clusters of molecules and partially remains as unassociated molecules. These clusters consist of two or more molecules in association and may consist of a large number of molecules. For the cluster with n molecules, $$nB \leftrightarrows B_n \qquad 2)$$

for which there is an equilibrium constant, $k_n$:

$$k_n = \frac{[B_n]}{[B]^n} \qquad 3)$$

where n is the number of individual molecules of B (monomer) which associate to form an cluster. [B] is the molar concentration of the monomers, and $[B_n]$ is the molar concentration of clusters of n monomers.

In mixtures of unlike molecules, $k_n$ can be considered an average. The thermodynamic equilibrium constant, defined as $(k_n)_T$, based on activities, or mole fractions, is constant. The equilibrium constant $k_n$, based on concentrations, is also constant as long as the concentrations are low enough to correspond to small mole fractions. For this case, the mole fraction X and the molar concentration, $C_M$, in mol/l are related by:

$$X = \frac{C_M(MW_s)}{1000\rho_s} \qquad 4)$$

where $MW_S$ is the molecular weight of the solvent and $\rho_S$ is the density of the solvent in g/cm³. Thus, $k_n$ and $(k_n)_T$ are related as follows:

$$(k_n)_T = k_n \left( \frac{1000\rho_s}{MW_s} \right) \qquad 5)$$

Define $R_n$ as the fraction of monomers that actually associate into clusters with n molecules. Then, $$[B_n] = \frac{B_o R_n}{n} \qquad 6)$$

and $$[B] = B_o Y \qquad 7)$$

where Y is defined as $$Y = 1 - \sum_{i=1}^{\infty} R_i \qquad 8)$$

and $B_0$ is the concentration of B if there is no association.

Define $MW_0$ as the molecular weight of the monomer B. $MW_0$ would be an average for a mixture of unlike molecules. Then C, the concentration of the solute in gram/liter, is:

$$C = B_0(MW_o) \quad 9)$$

Now, equations 6), 7), and 9) together are used in the equilibrium equation 3) to give $R_n$ in terms of C and the parameters n, $k_n$, and $MW_0$:

$$R_n = \frac{nk_n}{(MW_o)^{n-1}} Y^n C^{n-1} \quad 10)$$

Then, from the definition of Y (equation 8)), Y can be obtained as the solution to the following equation:

$$1 - Y = \sum_{i=2}^{m} \frac{ik_i}{(MW_o)^{i-1}} Y^i C^{i-1} \quad 11)$$

Where m=∞. Now, with Y known, all $R_n$ are calculated with equation 10).

Now, the apparent molecular weight, MW, is defined as the mass/number-of-particles, or:

$$MW = \frac{B_0(MW_0)V}{[B]V + \sum_{i=2}^{\infty}[B_i]V} \quad 12)$$

where V is the volume of the sample.

Using equations 6), and 7) in equation 12) gives $$MW = \frac{MW}{Y + \sum_{i=2}^{m}\frac{R_i}{i}} \quad 13)$$

where m=∞.

Finally, in order to carry out the calculations, some relationship between $k_n$ and n must be assumed.

$$k_n = f(n, a_1, a_2, \ldots, a_j) \quad 14)$$

In this generalized equation form, j is the number of constants of the relationship. Theoretically, $\Delta G_n$ is expected to increase (in absolute value) with increasing n and to be zero when n=1. A simple, yet versatile equation form for 14) suggested by these fundamental considerations is:

$$\ln(k_n) = a_1(n-1)^{a_2} \quad 15)$$

Values for the unknown constants, $a_1$ and $a_2, \ldots a_j$, along with $MW_0$ are obtained by fitting MW vs. C data to equations 10), 11), and 13) of the BRD method. The values for n may be any value 2 or greater, up to ∞, but for practical applications a maximum practical value, m, is chosen. Thus, the summations in actual practice are not carried to m=infinity as shown in the previous equations but to a practical value of m. A minimum of 3 data pairs are needed for the case using equation 15), but preferably more data pairs are fitted using least squares regression analysis. If a relationship with more constants than equation 15) is chosen for equation 14), then the BRD method will give the values for these constants and $MW_0$ as long as there are at least as many independent data pairs as unknowns (# of $a_n$ constants+1 (for $MW_0$)).

The BRD method may be simplified by assuming that only one (average) size cluster is formed, i.e., where n is assumed to be constant. For this case, only one $k_n$ is involved (equation 3)), and there is only one R at a given C. In the simplified form, equations 10) and 13) give C and MW as:

$$C = \left[\frac{R_n(MW_0)^{n-1}}{nk_n(1-R_n)^n}\right]^{\frac{1}{1-n}} \quad 16)$$

and $$MW = \frac{MW_0}{1 - R_n + \frac{R_n}{n}} \quad 17)$$

A fit of MW vs. C data to the simplified BRD method gives $MW_0$, an average n, and an average $k_n$. The simplified form can be used to establish an average value for n from which a maximum practical value for m in the extended method is estimated, typically 2 to 3 times the calculated n in the simplified method.

The BRD method relates true molecular weight of the monomer to the apparent molecular weight of the associated system in terms of a thermodynamically defined $k_n$ and a measure of the degree of association, n. In the simplified method, the values are average values. In the extended method, these values vary over a population of clusters and this variation is described by equation 14).

EXAMPLES OF APPLICATION

The BRD method can be used to calculate the true molecular weight of a solute in solution. To calculate the true molecular weight ($MW_0$) data are needed of the apparent molecular weight MW as a function of concentration of solute. This is conveniently obtained using vapor pressure osmometry methods. In vapor pressure osmometry, the temperature depression is related to the number of particles of solute whether monomer or associated cluster. The simplified BRD method is used in the following examples.

Example 1

VPO data were obtained on two samples of shale oil distillate using toluene as the solvent. Four data pairs of apparent molecular weight and concentrations were used. The data are used to find the best fit to equations 16) and 17) using least squares regression analysis.

Results are given in FIG. 1 for a nominal 275°–400° C. shale oil distillate. The BRD results calculate an average molecular weight for the monomer of 235 Dalton. The calculated n is 1.96 and the calculated $k_n$ is 3.5 (moles/liter)$^{-.96}$. A value of $(k)_T$=30.4 is calculated from Equation 5) (toluene solvent at 60° C.). From this a free energy of association, $\Delta G$, of −1163 cal/mole of monomer is calculated.

The measured average molecular weight by gc-ms is 232 Dalton. By traditional means of linear extrapolation of the VPO MW vs. C data, a value of 245 Dalton is determined. The low values for n and $k_n$ show that the system is not highly associated and the apparent molecular weight is not very different from the true molecular weight.

Example 2

In FIG. 2, a very different situation is observed for a 200°–275° C. distillate. Here, because of apparent acid-base reactions, a highly associated state is seen. The traditional method estimates a molecular weight of 735 for a system that by gc-ms has an actual average molecular weight of 173. In this case, the BRD method found a local minimum in the least squares expression fit of data at which the monomer molecular weight is 172. The agreement between these two numbers is partly fortuitous as the least squares residuals show that the fit for the data is not that precise. Nevertheless, no other local minimums were found.

The value for n is 7.8 and the calculated value for $k_n$ is $1.9 \times 10^{19}$ (moles/liter)$^{-6.8}$. From this data, a $(k_n)_T$ value of $9 \times 10^{25}$ is calculated which corresponds to a $\Delta G$ of $-5096$ cal/mole of monomer. The values for $\Delta G$ are in the known range of heats-of-fusion for polar aromatic types expected to comprise the associated particle.

The horizontal line at near-zero concentrations (FIG. 2) is a real consequence of the simplified method and is seen in cases where n is greater than about 3 or 4. For extremely low concentrations (C) the value for R also becomes small. At these limits, the BRD method becomes approximately:

$$\frac{MW}{MW_0} = 1 + \left(\frac{C}{C^*}\right)^{n-1} \qquad 18)$$

where $$C^* = \left[\frac{(MW_0)^{n-1}}{k_n(n-1)}\right] \qquad 19)$$

Where n is large and C remains sufficiently less than $C^*$, equation 18) describes a very nearly horizontal line. This horizontal line would not be seen in the extended method described previously.

Example 3

A fraction of >400° C. shale oil was dewaxed and the dewaxed oils were subjected to pentane deasphalting (40/1). VPO data were obtained and the simplified BRD method was applied to the data. Results are shown in FIG. 3.

The BRD results indicate an average molecular weight for the monomer of 583 Dalton. An independent measurement of the true molecular weight is not available. For these shale oil asphaltenes, the calculated n is 2.4 and the calculated $k_n$ is 153 (moles/liter)$^{-1.4}$. A value for the $(k_n)_T$ is calculated as 3159. From this, a free energy of association, $\Delta G$, of $-2285$ cal/mole of monomer is calculated.

DISCUSSION OF PREFERRED EMBODIMENTS

The BRD method thermodynamically characterizes associations that are strong enough to affect the number of particles seen in solution. A test of the method, using VPO as a tool for measuring the degree (n) and strength ($k_n$) of associations shows close agreement with independent measures and yields thermodynamic values in keeping with known association behavior.

In all non-pure compound systems, the solution is comprised of molecules with varying thermodynamic behavior (variable $k_n$ values). Likewise, the clusters are comprised of a variable number of solute molecules (n). A mathematical formulation of this phenomena is argued in the mathematical description above.

The method offers a powerful means for studying solution chemistry. Calculation of $\Delta H_n$ and $\Delta S_n$ of association can be made by measuring $k_n$ values at several different temperatures. Several $(k_n)_T$ calculated from equation 5) at these different temperatures are used to calculate $\Delta H_n$ and $\Delta S_n$. Other thermodynamic properties can be calculated from known thermodynamic relationships. These thermodynamic values can, in turn, be correlated with the electronic and geometric structure of the association, respectively. Variations of values for average n with differing solvent systems could shed light on solvent-solute interactions.

The techniques used for measuring associations need not be limited to VPO. Cryogenic, ebulioscopic viscometric, molecular filtration and perhaps optical or spectroscopic techniques may be applied. Common to any applicable technique its the ability to take a measurement of the associated system at differing concentrations, and from the association parameter values, calculate the true molecular weight of the disassociated system.

The method is expected to have applications wherever molecular association/precipitation and possibly adsorption are important to the analytical or process results. A generalized logic diagram for the BRD method is provided in FIG. 4. In this diagram values for n, $k_n$ and $MW_0$ may be obtained from experimental observation of apparent MW vs. concentration. Alternatively, it is possible to calculate average n, average k and average Rn from thermodynamic data, if such data is known. Once n, $k_n$ and $MW_0$ are known, a host of applications are possible. To illustrate, the following applications have been identified.

Analysis

The BRD method may be used to obtain true average molecular weights from data obtained by VPO and other techniques. The BRD method may be used to calculate $\Delta H$ and $\Delta S$ values for varying degrees of association. From this, it may be possible to infer which chemical types are associated into various cluster sizes. It may also be possible to correlate values of the method with properties such as viscosity, density, heat capacity, coefficient of thermal expansion and any other properties relatable to the association of molecules.

Blending

The BRD method may be used to optimize blending of process streams and to ascertain compatibility of streams. The method can provide $k_n$ as a function of n for the blending of the two streams, one of which is considered the solvent and the other is considered the solute. Blending ratios can then be determined that correspond to a highly dissociated case or a highly associated limit bordering on precipitation. Furthermore, applying the BRD method at various temperatures would give $\Delta H_n$ and $\Delta S_n$ so that dissociation and precipitation blending limits can be determined at various temperatures.

Design and Engineering

The BRD method may be used to assist in the design and engineering of chemical or petroleum processes. The BRD method provides $MW_0$, $\Delta H_n$ and $\Delta S_n$, which gives some indication of chemical types and molecular sizes in a stream. This is necessary information for the engineer who must select temperature, pressure, mixing ratios, catalyst types, residence times, vessel sizes, etc., so a piece of equipment will handle the stream in the way desired. Because of the thermodynamic relationships that exist between phase changes, the $\Delta H_n$ and $\Delta S_n$ data may be used in secondary correlations incorporated in process/kinetic methods.

Optimization

The BRD method may be used to assist in the economic optimization of process units and process sequences. The BRD method can be used to obtain n and $k_n$ for a specific solute dissolved in various solvents. The results could indicate which solvent types favor highly dissociated states (low n) and which favor highly associated states (high n) or precipitation (very high n). Chemical type and molecular weight of solvent can be variables about which to optimize for the desired degree of association. Furthermore, blending ratios for various solvents can be another variable in the optimization and the BRD method can accommodate this.

Processing

The BRD method may be used to describe or predict adsorption or stream properties extrapolatable to process correlations. The BRD method may be used to interpret and predict behavior in separation processes such as gel permeation chromatography and liquid-liquid extraction, liquid-solid adsorption and precipitations processing.

The BRD method provides $MW_0$, $\Delta H_n$ and $\Delta S_n$, which gives some indication of chemical types and molecular sizes in a stream. These are useful in estimating physical properties of a stream under processing conditions and the behavior of that stream in a reactor and in the presence of a catalyst or in other types of processing environments. These include those where precipitation may be required or where it must be avoided. For a given solute molecule, there is often a relationship between the thermodynamic properties of phase changes such as vaporization, adsorption and precipitation. The thermodynamic values obtained from the BRD method can be used for estimating thermodynamic behavior of phase changes.

Production

The BRD method may be used to study and possibly control fluids in petroleum production. The approaches used for predicting viscosities, solubilities, blending and compatibility discussed above may be used to design and control injection and production of petroleum from reservoirs.

Numerous other applications are possible based on the teachings of this invention. It is the purpose of this invention to include all applications which rely on the BRD method in whole, or in part, for their study, resolution, control, design or engineering.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method for calculating thermodynamic and molecular properties of molecules of a substance dissolved in a solvent in the liquid state, which method comprises:
   (a) maintaining a sample portion of the substance at a concentration (C) in the solvent,
   (b) measuring apparent molar concentration ($C_M$) at the actual concentration (C) to produce a data pair C vs. $C_M$, the apparent molar concentration determined by a method in list consisting of:
      (1) measuring the deviation of vapor pressure and saturation temperature of the sample from that of the pure solvent,
      (2) measuring the deviation of the melting point of a sample portion from that of the pure solvent,
   (c) defining an average aggregate mass ($M_A$) using the relation:

$$M_A = C/C_M$$

where the average aggregate mass ($M_A$) is the average molecular mass of clusters of associated molecules and any unassociated molecules, (d) repeating steps (a) through (c) for m repetitions with a different concentration (C) for each repetition to produce a set of data points of concentration (C) vs. average aggregate mass ($M_A$).
   (e) solving for $a_1, a_2, \ldots a_j$, and $MW_0$ from the C and $M_A$ data points from the following set of equations:
   a subset of equations for n=2 to m defined by $$R_n = \frac{nk_n}{(MW_0)^{n-1}} Y^n C^{n-1}$$

an equation defined by $$1 - Y = \sum_{i=2}^{m} \frac{ik_i}{(MW_0)^{i-1}} Y^i C^{i-1}$$

an equation defined by $$M_A = \frac{MW_0}{Y + \sum_{i=2}^{m} \frac{R_i}{i}}$$

and a subset of equations that are relations between $k_n$ and n, for n=2 to m $$k_n = f(n, a_1, a_2, \ldots, a_j)$$

where:
   $MW_0$ is the average molecular weight of the substance molecule,
   m is an integer greater than 2,
   $k_n$ for n=2 to m are equilibrium constants of association between monomers of the substance and clusters of monomers,
   $a_1, a_2, \ldots a_j$ are constants,
   and j is an integer greater than 0,
   the number (m) of the apparent mass ($M_A$) versus concentration (C) data points produced by the repetitions in step (e) being an integer greater than j.

2. The method of claim 1 wherein thermodynamic properties are determined from the values of $k_n$.

3. The method of claim 1 additionally comprising repeating steps (a) through (e) at a different temperature of the sample portion to produce a plurality of subsets of equation sets $k_n$.

4. The method of claim 3 wherein thermodynamic properties are determined from the values of $k_n$.

5. A method for calculating thermodynamic and molecular properties in molecules of a substance dissolved in a solvent in the condensed state, which method comprises:
   (a) maintaining a sample portion of the substance at a concentration (C) in the solvent,
   (b) measuring apparent molar concentration ($C_M$) at the actual concentration (C) to produce a data pair C vs. $C_M$, the apparent molar concentration determined by measuring the deviation of vapor pressure and saturation temperature,
   (c) defining an average aggregate mass ($M_A$) using the relation:

$$M_A = C/C_M$$

where the average aggregate mass ($M_A$) is the average molecular mass of clusters of associated molecules and any unassociated molecules, (d) repeating steps (a) through (c) for m repetitions with a different concentration (C) for each repetition to produce a set of data points of concentration (C) vs. average aggregate mass ($M_A$).

(e) solving for $a_1, a_2, \ldots a_j$, and $MW_0$ from the C and $M_A$ data points from the following set of equations:
a subset of equations for n=2 to m defined by $$R_n = \frac{nk_n}{(MW_0)^{n-1}} Y^n C^{n-1}$$

an equation defined by $$1 - Y = \sum_{i=2}^{m} \frac{ik_i}{(MW_0)^{i-1}} Y^i C^{i-1}$$

an equation defined by $$M_A = \frac{MW_0}{Y + \sum_{i=2}^{m} \frac{R_i}{i}}$$

and a subset of equations that are relations between $k_n$ and n, for n=2 to m $$k_n = f(n, a_1, a_2, \ldots, a_j)$$

where:
$MW_0$ is the average molecular weight of the substance molecule.
m is an integer greater than 2.
$k_n$ for n=2 to m are equilibrium constants of association between monomers of the substance and clusters of monomers.
$a_1, a_2, \ldots a_j$ are constants.
and j is an integer greater than 0.
the number (m) of the average aggregate mass ($M_A$) versus concentration (C) data points produced by the repetitions in step (e) being an integer greater than j.

6. The method of claim 5 wherein thermodynamic properties are determined from the values of $k_n$.

7. The method of claim 5 additionally comprising repeating steps (a) through (e) at a difference temperature of the sample portion to produce a plurality of subsets of equation sets $k_n$.

8. The method of claim 7 wherein thermodynamic properties are determined from the values of $k_n$.

9. A method for calculating thermodynamic and molecular properties in molecules of a substance dissolved in a solvent in the condensed state, which method comprises:

(a) maintaining a sample portion of the substance at a concentration (C) in the solvent.

(b) measuring apparent molar concentration ($C_M$) at the actual concentration (C) to produce a data pair C vs. $C_M$, the apparent molar concentration determined by measuring the deviation of melting point.

(c) defining an average aggregate mass ($M_A$) using the relation:

$$M_A = C/C_M$$

where the average aggregate mass ($M_A$) is the average molecular mass of clusters of associated molecules and any unassociated molecules.

(d) repeating steps (a) through (c) for m repetitions with a different concentration (C) for each repetition to produce a set of data points of concentration (C) vs. average aggregate mass ($M_A$).

(e) solving for $a_1, a_2, \ldots a_j$, and $MW_0$ from the C and $M_A$ data points from the following set of equations:
a subset of equations for n=2 to m defined by $$R_n = \frac{nk_n}{(MW_0)^{n-1}} Y^n C^{n-1}$$

an equation defined by $$1 - Y = \sum_{i=2}^{m} \frac{ik_i}{(MW_0)^{i-1}} Y^i C^{i-1}$$

an equation defined by $$M_A = \frac{MW_0}{Y + \sum_{i=2}^{m} \frac{R_i}{i}}$$

and a subset of equations that are relations between $k_n$ and n, for n=2 to m $$k_n = f(n, a_1, a_2, \ldots, a_j)$$

where:
$MW_0$ is the average molecular weight of the substance molecule.
m is an integer greater than 2.
$k_n$ for n=2 to m are equilibrium constants of association between monomers of the substance and clusters of monomers.
$a_1, a_2, \ldots a_j$ are constants.
and j is an integer greater than 0.
the number (m) of the average aggregate mass ($M_A$) versus concentration (C) data points produced by the repetitions in step (e) being an integer greater than j.

10. The method of claim 9 wherein thermodynamic properties are determined from the values of $k_n$.

11. The method of claim 9 additionally comprising repeating steps (a) through (e) at a different temperature of the sample portion to produce a plurality of subsets of equation sets $k_n$.

12. The method of claim 11 wherein thermodynamic properties are determined from the values of $k_n$.

* * * * *